United States Patent
Biedermann et al.

(10) Patent No.: US 9,345,516 B2
(45) Date of Patent: May 24, 2016

(54) POLYAXIAL BONE ANCHORING DEVICE

(75) Inventors: Timo Biedermann, Trossingen (DE); Lutz Biedermann, VS-Villingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 328 days.

(21) Appl. No.: 13/588,859

(22) Filed: Aug. 17, 2012

(65) Prior Publication Data

US 2013/0096622 A1     Apr. 18, 2013

Related U.S. Application Data

(60) Provisional application No. 61/525,093, filed on Aug. 18, 2011.

(30) Foreign Application Priority Data

Aug. 18, 2011    (EP) ..................................... 11178034

(51) Int. Cl.
    *A61B 17/70*        (2006.01)
    *A61B 17/86*        (2006.01)

(52) U.S. Cl.
    CPC ............. *A61B 17/70* (2013.01); *A61B 17/7035* (2013.01); *A61B 17/8605* (2013.01)

(58) Field of Classification Search
    CPC .............. A61B 17/70; A61B 17/7001; A61B 17/7032; A61B 17/7034; A61B 17/7035; A61B 17/7037; A61B 17/7038; A61B 17/704; A61B 17/7041; A61B 17/7043; A61B 17/7046
    USPC ............ 606/60, 246–279, 300–320, 325–328
    See application file for complete search history.

(56) References Cited

U.S. PATENT DOCUMENTS 5,067,955 A * 11/1991 Cotrel ................ A61B 17/7034
                                        411/398
5,593,407 A * 1/1997 Reis .................... A61B 17/7055
                                        606/261

(Continued)

FOREIGN PATENT DOCUMENTS

CN           1965769 A      5/2007
CN        101909536 A     12/2010

(Continued)

OTHER PUBLICATIONS

Extended European Search Report for European Application No. 11178034.2, extended European Search Report dated Dec. 5, 2011 and mailed Dec. 19, 2011 (7 pgs.).

*Primary Examiner* — Pedro Philogene
*Assistant Examiner* — Lynnsy Summitt
(74) *Attorney, Agent, or Firm* — Lewis Roca Rothgerber Christie, LLP (57) ABSTRACT

A polyaxial bone anchoring device includes an anchoring element having a shaft and a head, a receiving part having a first end and a second end, a bore extending from the first end towards the second end, a seat for receiving the head, and at least one threaded through hole transverse to the bore, a pressure element to exert pressure onto the head, such that the head is pivotable and can be locked at an angle relative to the receiving part, the pressure element having at least one hole configured to at least partially align with the through hole, and at least one set screw threadable into the through hole to engage the pressure element at the hole such that a force is exerted by the pressure element onto the head that maintains the head at an adjustable angular position relative to the receiving part by friction.

20 Claims, 9 Drawing Sheets

(56) References Cited

U.S. PATENT DOCUMENTS

| | | | |
|---|---|---|---|
| 5,681,319 A | 10/1997 | Biedermann et al. | |
| 5,716,356 A | 2/1998 | Biedermann et al. | |
| 5,989,254 A * | 11/1999 | Katz | A61B 17/7038 606/308 |
| 6,368,321 B1 * | 4/2002 | Jackson | A61B 17/7035 606/270 |
| 6,440,137 B1 * | 8/2002 | Horvath | A61B 17/7037 606/302 |
| 6,736,820 B2 * | 5/2004 | Biedermann | A61B 17/7037 606/308 |
| 6,837,889 B2 * | 1/2005 | Shluzas | A61B 17/7037 606/267 |
| 6,964,666 B2 * | 11/2005 | Jackson | A61B 17/7035 606/264 |
| 7,087,057 B2 * | 8/2006 | Konieczynski | A61B 17/8605 606/278 |
| 7,144,396 B2 * | 12/2006 | Shluzas | A61B 17/7037 606/266 |
| 7,604,656 B2 * | 10/2009 | Shluzas | A61B 17/7037 606/270 |
| 7,678,139 B2 * | 3/2010 | Garamszegi | A61B 17/7011 606/266 |
| 7,722,652 B2 * | 5/2010 | Justis | A61B 17/7035 606/267 |
| 8,012,183 B2 * | 9/2011 | Alain | A61B 17/7037 606/264 |
| 8,038,701 B2 * | 10/2011 | Rock | A61B 17/7032 606/266 |
| 8,137,387 B2 * | 3/2012 | Garamszegi | A61B 17/7032 606/270 |
| 8,157,843 B2 * | 4/2012 | Biedermann | A61B 17/7031 606/255 |
| 8,267,980 B2 * | 9/2012 | Felix | A61B 17/7037 606/306 |
| 8,273,112 B2 * | 9/2012 | Garamszegi | A61B 17/7011 606/266 |
| 8,287,576 B2 * | 10/2012 | Barrus | A61B 17/7032 606/300 |
| 8,308,776 B2 * | 11/2012 | Abdou | A61B 17/8685 606/279 |
| 8,377,101 B2 * | 2/2013 | Barrus | A61B 17/7037 606/264 |
| 8,398,689 B2 * | 3/2013 | Abdou | A61B 17/8685 606/300 |
| 8,409,260 B2 * | 4/2013 | Biedermann | A61B 17/7037 606/301 |
| 8,449,578 B2 * | 5/2013 | Keiser | A61B 17/7032 606/264 |
| 8,480,711 B2 * | 7/2013 | Garamszegi | A61B 17/7032 606/246 |
| 8,556,941 B2 * | 10/2013 | Hutchinson | A61B 17/7038 606/279 |
| 8,568,458 B2 * | 10/2013 | Matthis | A61B 17/7032 606/264 |
| 8,632,571 B2 * | 1/2014 | Kraus | A61B 17/7032 606/264 |
| 8,657,858 B2 * | 2/2014 | Garamszegi | A61B 17/7037 606/278 |
| 2003/0167058 A1 | 9/2003 | Shluzas | |
| 2004/0138662 A1 | 7/2004 | Landry et al. | |
| 2004/0204711 A1 | 10/2004 | Jackson | |
| 2006/0293665 A1 | 12/2006 | Shluzas | |
| 2007/0161996 A1 | 7/2007 | Biedermann et al. | |
| 2007/0191835 A1 * | 8/2007 | Justis | A61B 17/7035 606/279 |
| 2007/0233078 A1 * | 10/2007 | Justis | A61B 17/7035 606/279 |
| 2007/0270813 A1 * | 11/2007 | Garamszegi | A61B 17/7032 606/278 |
| 2008/0269809 A1 * | 10/2008 | Garamszegi | A61B 17/7037 606/305 |
| 2009/0312804 A1 * | 12/2009 | Gamache | A61B 17/704 606/308 |
| 2010/0063550 A1 * | 3/2010 | Felix | A61B 17/7032 606/301 |
| 2010/0094349 A1 * | 4/2010 | Hammer | A61B 17/7034 606/264 |
| 2010/0114171 A1 * | 5/2010 | Boachie-Adjei | A61B 17/7008 606/264 |
| 2010/0160978 A1 * | 6/2010 | Carbone | A61B 17/866 606/305 |
| 2010/0234902 A1 * | 9/2010 | Biedermann | A61B 17/7037 606/305 |
| 2010/0262196 A1 * | 10/2010 | Barrus | A61B 17/7037 606/308 |
| 2010/0292740 A1 | 11/2010 | Garamszegi et al. | |
| 2012/0046699 A1 * | 2/2012 | Jones | A61B 17/7037 606/305 |
| 2012/0136395 A1 * | 5/2012 | Biedermann | A61B 17/7037 606/279 |
| 2012/0143265 A1 * | 6/2012 | Biedermann | A61B 17/7035 606/328 |
| 2012/0150239 A1 * | 6/2012 | Garamszegi | A61B 17/7032 606/328 |
| 2013/0046345 A1 * | 2/2013 | Jones | A61B 17/7037 606/266 |
| 2013/0079830 A1 * | 3/2013 | Garamszegi | A61B 17/7011 606/305 |
| 2013/0079831 A1 * | 3/2013 | Biedermann | A61B 17/8863 606/305 |
| 2013/0096624 A1 * | 4/2013 | Di Lauro | A61B 17/7011 606/279 |
| 2013/0150904 A1 * | 6/2013 | Biedermann | A61B 17/84 606/328 |
| 2013/0197583 A1 * | 8/2013 | Arnold | A61B 17/7004 606/264 |
| 2013/0197586 A1 * | 8/2013 | Matthis | A61B 17/7035 606/278 |
| 2013/0268006 A1 * | 10/2013 | Garamszegi | A61B 17/7032 606/266 |
| 2013/0338721 A1 * | 12/2013 | Biedermann | A61B 17/7037 606/305 |
| 2014/0025119 A1 * | 1/2014 | Biedermann | A61B 17/7032 606/266 |
| 2014/0172023 A1 * | 6/2014 | Garamszegi | A61B 17/7032 606/305 |

FOREIGN PATENT DOCUMENTS

| | | |
|---|---|---|
| EP | 221012 A1 | 8/2010 |
| WO | WO 2009/055747 A1 | 4/2009 |

* cited by examiner

POLYAXIAL BONE ANCHORING DEVICE

CROSS-REFERENCE TO RELATED APPLICATION(S)

The present application claims the benefit of U.S. Provisional Patent Application Ser. No. 61/525,093, filed Aug. 18, 2011, the contents of which are hereby incorporated by reference in their entirety, and claims priority to European Patent Application EP 11 178 034.2, filed Aug. 18, 2011 the contents of which are hereby incorporated by reference in their entirety.

BACKGROUND

1. Field of the Invention

The invention relates to a polyaxial bone anchoring device for anchoring a stabilization rod relative to a bone or a vertrebra. The bone anchoring device includes an anchoring element, a receiving part for receiving a head of the anchoring element and for receiving a stabilization rod to be connected to the anchoring element. The anchoring element is pivotably connected to the receiving part and can be locked at an angle by exerting pressure onto the head via a pressure element that is arranged in the receiving part. The pressure element and the receiving part are configured to cooperate in such a way that the pressure element can frictionally clamp the head to maintain a desired angular position before locking of the polyaxial bone anchoring device.

2. Description of Related Art

U.S. Pat. No. 5,716,356 describes a polyaxial bone screw including a screw element and a receiving part which is pivotably connected to the screw element and a pressure element to exert pressure onto the head of the screw element to lock the angle between the screw element and the receiving part. The receiving part has a U-shaped channel for receiving a stabilization rod. The pressure element comprises a cylindrical recess, which is to be aligned with the U-shaped channel to receive the rod therein. In order to hold the pressure element in a position aligned with the U-shaped channel, the position of the pressure element is fixed by crimping through bores provided in the receiving part.

However, when the head of the bone anchoring element remains freely pivotable with respect to the receiving part before locking the head in a final angular position, alignment of the receiving part and the insertion of the rod may be difficult in more complex clinical applications, for example, when a multitude of bone anchors have to be connected to the rod.

U.S. Pat. No. 7,604,656 (Shluzas) describes a fastener engageable with a bone portion to connect a longitudinal member to the bone portion. The housing that receives the fastener also receives a spacer, which is engageable with the fastener and the longitudinal member. In one embodiment, the spacer is urged by a pin member into frictional engagement with the fastener and with the housing.

SUMMARY

It is an object of the invention to provide a polyaxial bone anchoring device and a method for manufacturing the same which allows for improved handling during surgery and which can be manufactured in a simple manner.

With the polyaxial bone anchoring device according to embodiments of the invention, a temporary clamping of a head of an anchoring element in a desired angular position with respect to a receiving part, without locking the head, can be achieved. This allows maintaining of the receiving part in an adjustable angular position. In this condition, a pressure element exerts a preload onto the head, where the head is not locked, but is prevented from freely pivoting. When the head is temporarily clamped, alignment of the receiving part with respect to a rod and insertion of the rod is more easily facilitated, in particular, in situations in which a multitude of bone anchors are to be connected to the rod or rods.

Furthermore, when the rod is already inserted into the receiving part, adjustments of the rod are still possible without completely unlocking the head.

The polyaxial bone anchoring device according to embodiments of the invention comprises only few parts which are each of simple design, and where relatively large manufacturing tolerances are possible. A mechanism utilized to frictionally maintain the head before locking is free from any spring members or portions. This may facilitate easier manufacturing of the polyaxial bone anchoring device. Furthermore, existing receiving parts and pressure elements can be used without substantially modifying their forms. For example, it is possible to change existing crimp bores to threaded through bores.

An amount of preload exerted onto the head by the pressure element or member can be exactly predefined in a simple manner, for example, by selecting a position and shape of the bores and a shape of the set screw or screws, and furthermore by a force applied by the set screw or screws that is dependent on how deep the screws are advanced. By means of the set screws, a stepless adjustability of the pressure which is exerted on the head of the anchoring element is achievable. By screwing in the set screw tightly, for example, a polyaxial screw can be used as a monoaxial screw. Further, a friction force exerted by the set screws is reversible by loosening the set screws.

The polyaxial bone anchoring device according to embodiments of the invention can be provided to the surgeon in a pre-assembled manner, where the pressure element is axially and rotationally fixed by the set screw to such an extent that it can not fall out of the receiving part or be rotated out of its aligned position. This allows for safer insertion by a surgeon or other practitioner. It is also possible to provide receiving parts with pre-mounted set screws, which allows the surgeon to introduce the desired bone screw, to insert the pressure element into the receiving part, and to lock and/or clamp the polyaxial bone anchoring device by means of the set screw or the set screws.

The receiving part and the pressure element can be manufactured in series at low costs.

BRIEF DESCRIPTION OF THE DRAWINGS

Further features and advantageous of the invention will become apparent from the description of the embodiments by means of the accompanying drawings. In the drawings.

DETAILED DESCRIPTION

A polyaxial bone anchoring device 1 according to a first embodiment as shown in FIGS. 1 to 4 includes a bone anchoring element 2 in the form of a screw member having a threaded shaft 3 and a head 4. The head 4 is generally spherical and includes a recess 4a at its free end for engagement with a tool to insert the threaded shaft 3 into a bone. The bone anchoring device 1 further includes a receiving part 5 for connecting the anchoring element 2 to a rod 20. A pressure element 6 is arranged in the receiving part 5 on top of the head 4 (as seen, for example, in FIGS. 3 and 4). For securing the rod 20 in the receiving part 5, and in some embodiments, for exerting pressure onto the head 4, a locking device, for example an inner screw 7, which cooperates with the receiving part 5, is provided.

The receiving part is a substantially cylindrical one piece part and has a top end 51 and a bottom end 52. A passageway extending from the top end 51 to the bottom end 52 is formed by a coaxial bore 53 followed by a seat portion 54 for receiving the head 4 of the anchoring element 2. The seat portion 54 has an opening 55 at the bottom end 52 through which the shaft 3 of the anchoring element 2 extends. The seat portion 54 is shown to be spherically-shaped, but in other embodiments, the seat portion can be tapered or can have any other shape that allows the head 4 to be received so that the head 4 can pivot with respect to the receiving part 5. At the top end 51, a substantially U-shaped recess 56 is provided by means of which two free legs 57, 58 are formed that form sidewalls of a channel for receiving the rod 20. An internal thread 59 is provided at the legs 57, 58 for cooperating with the inner screw 7.

As can be seen from FIGS. 5 to 8, the pressure element 6 in this embodiment is formed in one piece. The pressure element 6 is of substantially cylindrical construction, and has an outer diameter which allows it to move in an axial direction within the bore 53 of the receiving part 5. The pressure element 6 has a top end 61 and a bottom end 62. When the pressure element 6 is inserted into the receiving part 5, the bottom end 62 faces the head 4 of an inserted anchoring element 2. At the bottom end 62, a spherical recess 63 is provided, which is adapted to the size and shape of the head 4. The spherical recess 63 is configured to come into frictional engagement with the spherical surface of the head 4. At the top end 61, a U-shaped recess 64 is provided by means of which two free legs 65, 66 are formed that form a channel to receive the rod 20 therein. Furthermore, the pressure element 6 includes a coaxial bore 67 for accessing the head 4 with a tool (not shown). The pressure element 6 may be a solid member, without any spring portions which could render it flexible. It is arranged in the receiving part 5 such that the U-shaped recess 56 of the receiving part 5 and the U-shaped recess 64 of the pressure element 6 are aligned.

Figure 1:
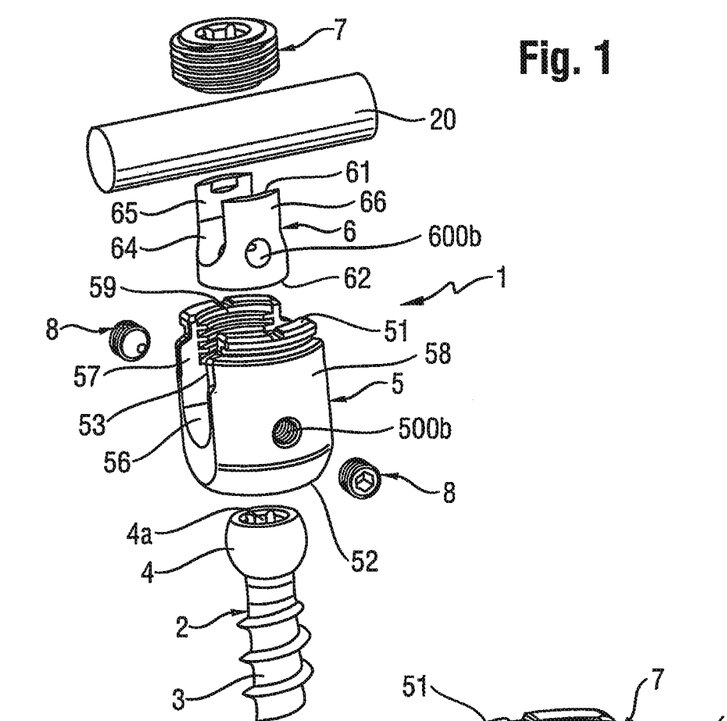
FIG. 1 shows a perspective exploded view of a polyaxial bone anchoring device according to a first embodiment.
Figure 2:
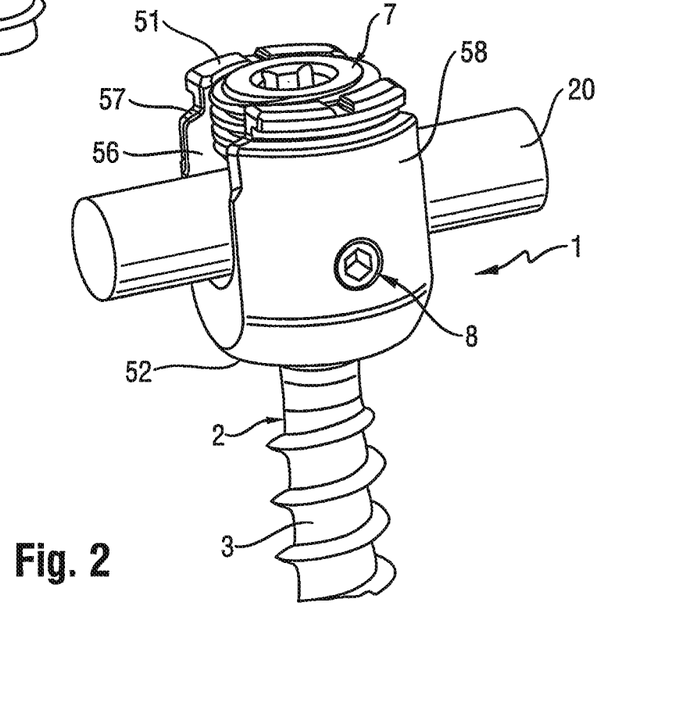
FIG. 2 shows the polyaxial bone anchoring device of FIG. 1 in an assembled state.
Figure 3:
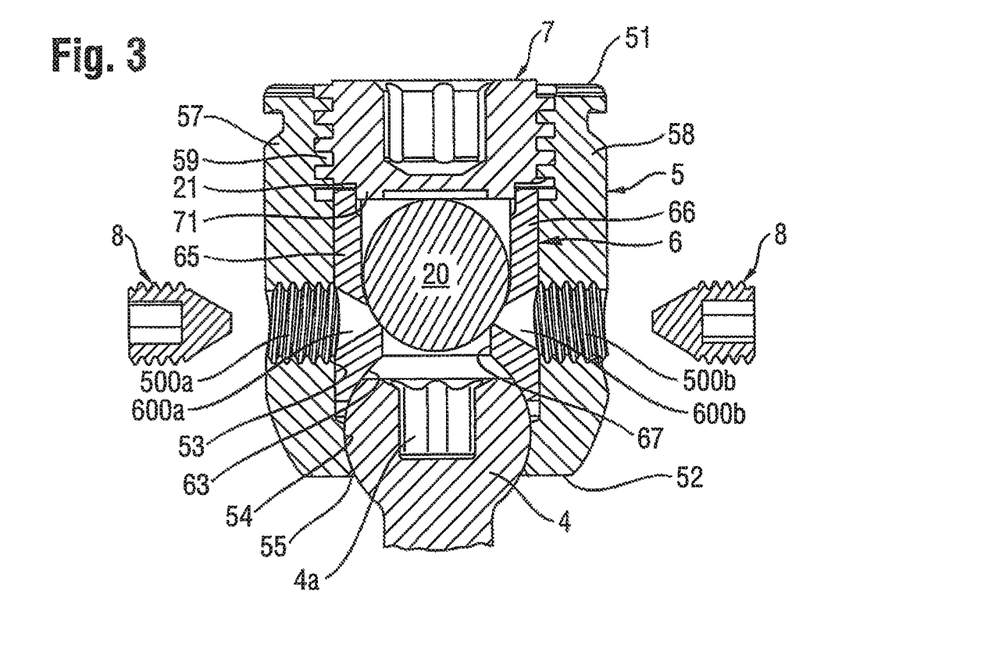
FIG. 3 shows a cross-sectional view of the polyaxial bone anchoring device of FIGS. 1 and 2 in an assembled state before final locking of the head, with two non-assembled set screws.

In FIG. 3, the head 4 of the anchoring element 2 is located in the seat 54 and the pressure element 6 is arranged on top of the screw head 4. The heights of the free legs 65, 66 of the pressure element 6 are configured such that the free legs 65, 66 extend above the rod 20 when the rod 20 is inserted and rests on a bottom of the channel of the pressure element 6. The two set screws 8 are in a non-assembled state in FIG. 3.

Figure 4:
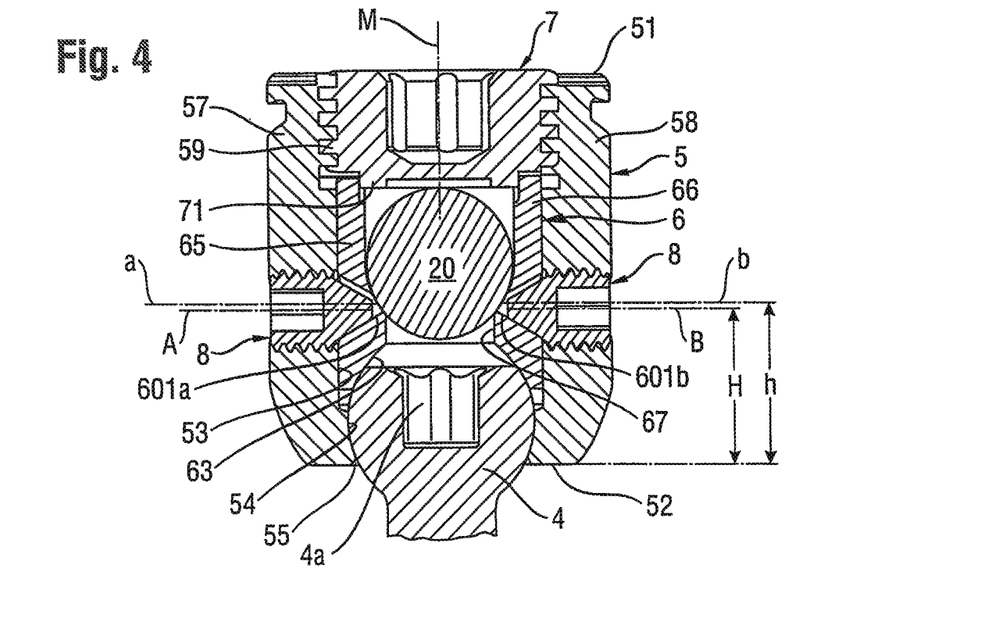
FIG. 4 shows a cross-sectional view of the polyaxial bone anchoring device of FIGS. 1 and 2 in an assembled state.
Figure 5:
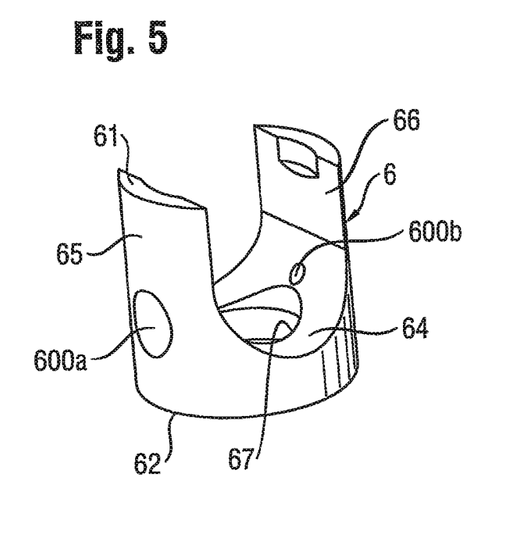
FIG. 5 shows a perspective top view of a pressure element according to an embodiment.
Figure 6:
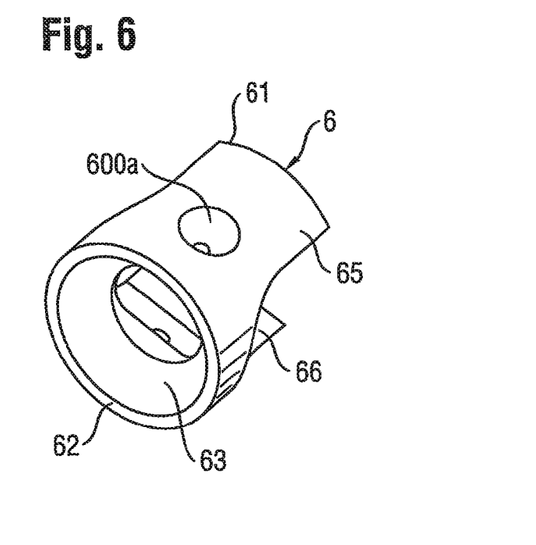
FIG. 6 shows a perspective bottom view of the pressure element of FIG. 5.
Figure 7:
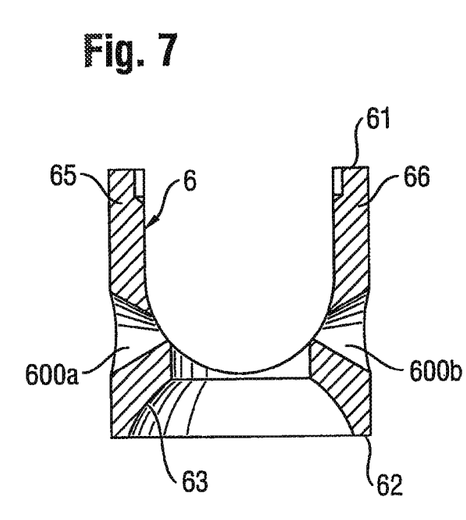
FIG. 7 shows a cross-sectional view of the pressure element of FIGS. 5 and 6.
Figure 8:
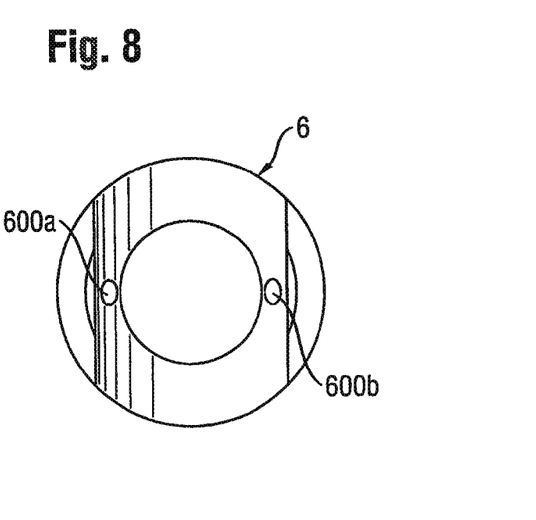
FIG. 8 shows a top view of the pressure element of FIGS. 5 and 6.
Figure 9:
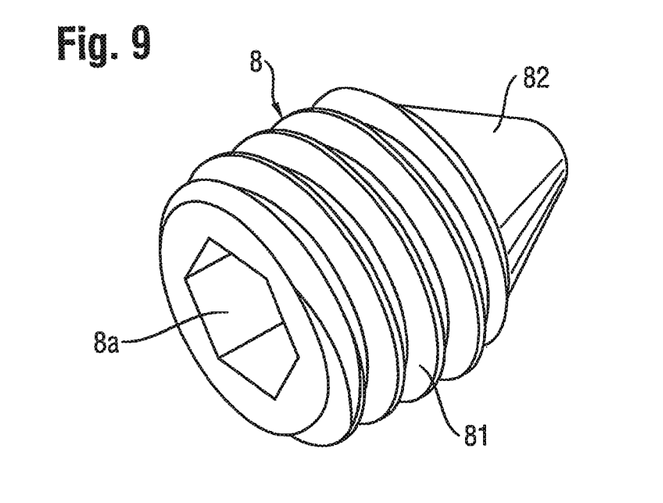
FIG. 9 shows a perspective view of a set screw according to an embodiment.
Figure 10:
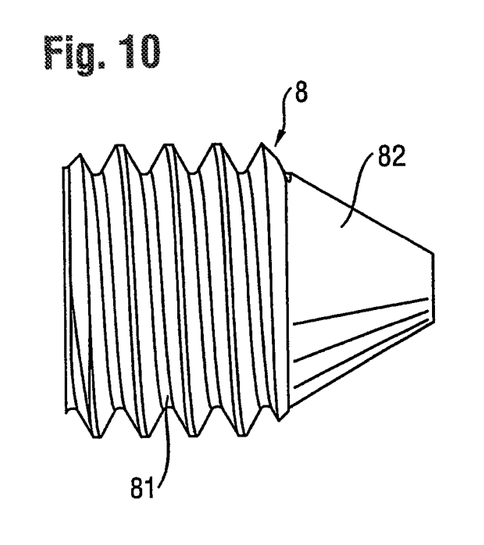
FIG. 10 shows a side view of the set screw of FIG. 9.
Figure 11:
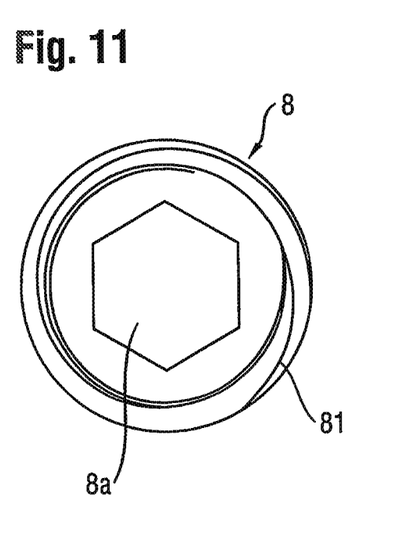
FIG. 11 shows a top view of the set screw of FIGS. 9 and 10.

In FIG. 4 the two set screws 8 are in an assembled state. As can be seen from FIGS. 9 to 11, the set screw (or grub screw) 8 is a headless screw having an outer thread 81, a first end, and a second end. On the first end, a engagement structure 8a for engagement with a tool (not shown), for example, a screw driver, is provided. In FIGS. 9 and 11, it can be seen that the engagement structure 8a is an internal hexagon for engagement with a hexagon socket screw key (not shown). However, any other socket or engagement structure may instead be formed on the set screws. The second end of the set screw 8 in this embodiment is a truncated cone-shaped or taper-shaped portion 82 having a flattened tip.

The locking device in the form of the inner screw 7 has a projection 71 extending into the channel formed by the free legs 65, 66 of the pressure element 6. A size of the projection 71 in an axial direction is such that when the inner screw 7 is tightened, the projection 71 presses onto the rod 20 while there is still a gap 21 between the top end 61 of the pressure element and a lower side of the inner screw 7. Therefore, with a single inner screw 7, pressure can be exerted onto the rod 20 only, which in turn can exert pressure onto the pressure element 6. It should be noted that, instead of the single part locking device in the form of the inner screw 7, in other embodiments, a two-part locking device can be used (not shown). Such a two-part locking device may include a first part to be screwed in between the legs 57, 58 of the receiving part, and which acts onto the top end 61 of the pressure element 6. Further, a second part in the form of an inner screw may be provided in the first part, which is configured to press onto the rod 20. By means of this, the head 4 and the rod 20 can be independently fixed relative to the receiving part 5.

The receiving part 5 includes two threaded through bore holes 500a, 500b extending from a outer surface of the receiving part 5 into the coaxial bore 53. The bore holes 500a, 500b may be arranged at 180° offset from each other on the receiving part 5 and at 90° with respect to the channel formed by the U-shaped recess 56. The bore holes 500a, 500b may be aligned perpendicular with respect to a bore axis M of the coaxial bore 53. The bore axes A and B of the bore holes 500a, 500b are provided at a distance H from the second end 52 of the receiving part 5.

The pressure element 6 according to this embodiment correspondingly includes two through bore holes 600a, 600b which are 180° offset from each other and 90° offset from the channel formed by the U-shaped recess 64. The bore holes 600a, 600b have center axes a, b, respectively, which are perpendicular to the bore axis M. In the embodiment shown, the bore holes 600a, 600b each have a conical shape. Downwardly extending flanks or surfaces 601a, 601b of the bore holes 600a, 600b may each be arranged at an angler β of approximately 60° with the central bore axis M. When the pressure element 6 is inserted and rests on the head 4 of the anchoring element 2, the central axes a, b of the bore holes 600a, 600b each has a distance h from the second end 52 of the receiving part 5 that is greater than the distance H of the bore axes A, B of the bore holes 500a, 500b. In other words, the bore holes 600a, 600b are arranged above the threaded bore holes 500a, 500b. In some embodiments, the bore holes of the pressure element 6 can be blind holes having open sides facing an inner wall of the receiving part 5.

A distance between the axes of the bore holes 600a, 600b and the axes of the bore holes 500a, 500b in an axial direction is such that when the set screws 8 are screwed into the bore holes 500a, 500b, the tapered surfaces of the set screws 8 press onto the lower surfaces 601a, 601b of the bore holes 600a, 600b, respectively, to exert a downward force onto the pressure element 6. The resulting force onto the pressure element 6 generates a preload onto the head 4, which clamps the head 4 by means of friction. By controlling the thread turning and advancement of the set screws 8, a desired friction force can be achieved. The screwing-in process can be force-actuated and/or path-controlled. By this friction force, the head 4 can be maintained in a desired angular position, and can be moved out of the position by applying a force greater than the friction force either on the anchoring element 2 or on the receiving part 5. Simultaneously, via the set screws 8, the pressure element 6 is secured against rotation and secured against escaping through the top end 51 of the receiving part 5. The bore holes 600a, 600b provide space for relative to cones of the set screws 8 for the pressure element 6 to move downward to finally lock the head 4.

Figures 12, 13:
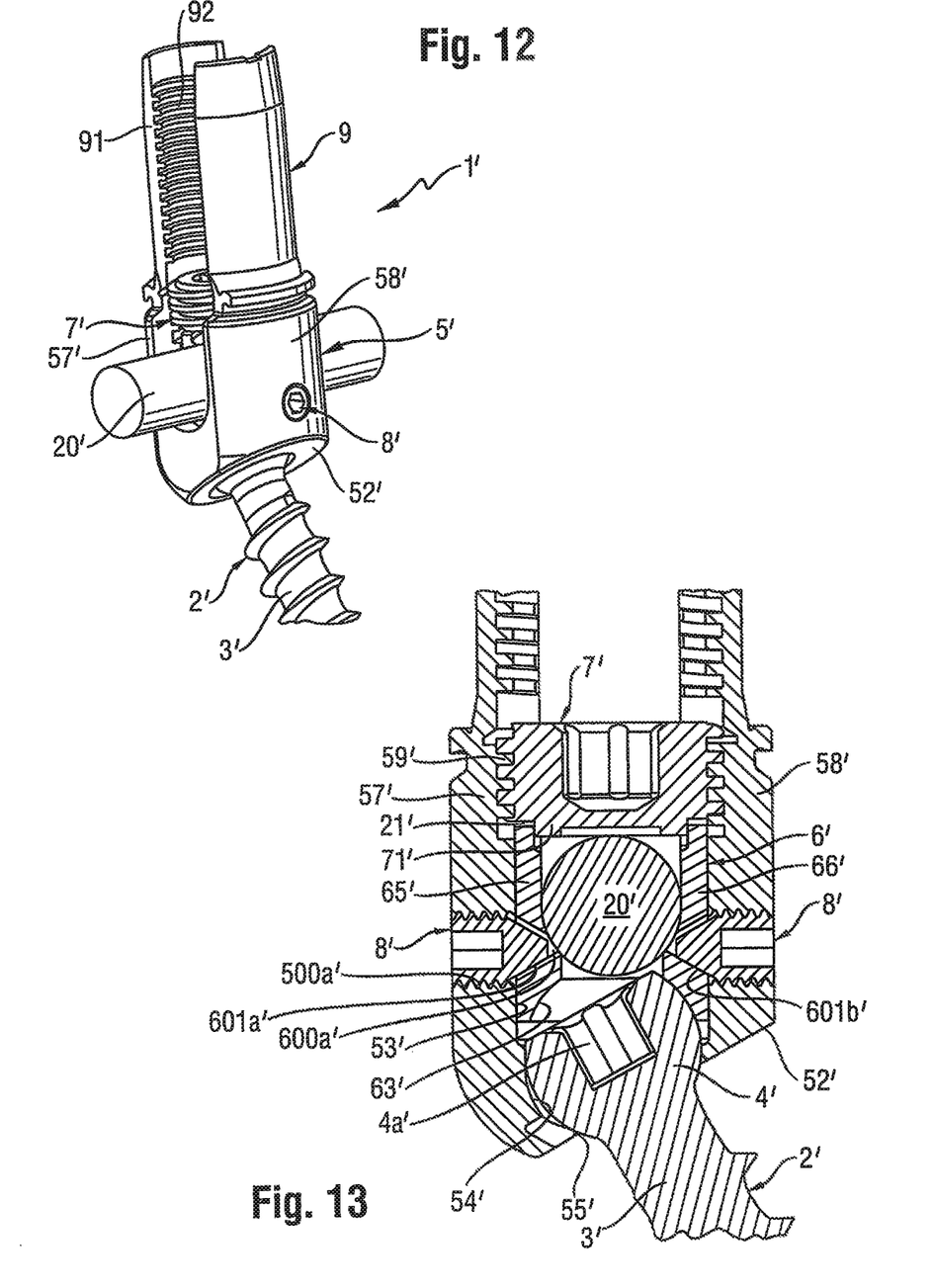
FIG. 12 shows a perspective view of a polyaxial bone anchoring device according to a second embodiment in an assembled state.
FIG. 13 shows a cross-sectional view of the polyaxial bone anchoring device of FIG. 12.

A second embodiment is shown in FIGS. 12 and 13. The only difference relative to the first embodiment is the shape of the receiving part 5'. The other parts of the bone anchoring device 1' are the same as or similar to those of the first embodiment, and the descriptions thereof shall not be repeated.

The receiving part 5' has an asymmetric bottom end 52' for allowing a greater pivot angle of the anchoring element 2' to one side. Such an asymmetric bottom end 52' can be achieved, for example, by cutting away a portion of the receiving part 5' at an inclined angle.

Furthermore, the receiving part 5' may be formed with a coaxial tube shaped extension 9 that has a slot 91 for inserting the rod 20' and an internal thread 92. Such an extension may be used for minimally invasive surgery, and can be broken away after tightening of the inner screw 7'.

It shall be noted that the shape of the set screws and/or the bore holes may also vary. In particular, the angle of the conical portion of the set screws may vary or the bottoms may have a rounded or other shape. The bore holes provided at the pressure element may also have various different shapes.

Figure 14:
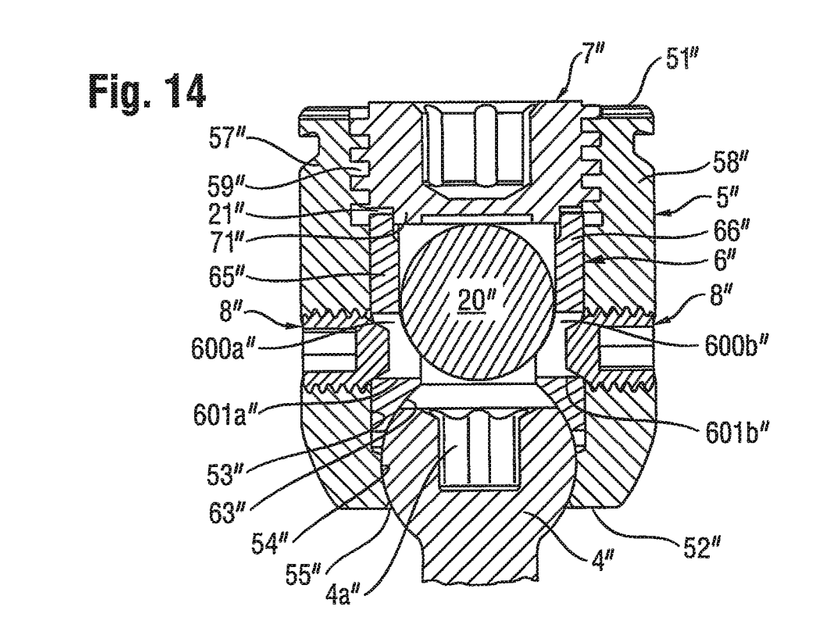
FIG. 14 shows a cross-sectional view of a polyaxial bone anchoring device according to a third embodiment in an assembled state.

According to a third embodiment, shown in FIG. 14, bore holes 600a", 600b" can have, for example, a substantially rectangular cross-section.

Figure 15:
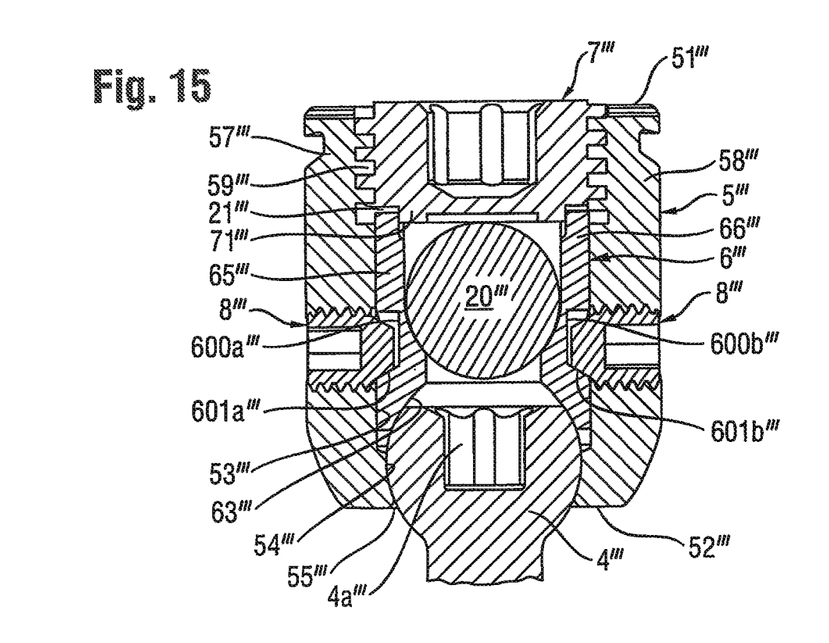
FIG. 15 shows a cross-sectional view of a polyaxial bone anchoring device according to a fourth embodiment in an assembled state.

According to a fourth embodiment. shown in FIG. 15, a cross-section of bore holes 600a''', 600b''' of the pressure element 6''' can be, for example, trapezoidal, with an inclined lower surface 601a''', 601b''' for engagement with truncated tapered surfaces of set screws 8'''.

Figure 16:
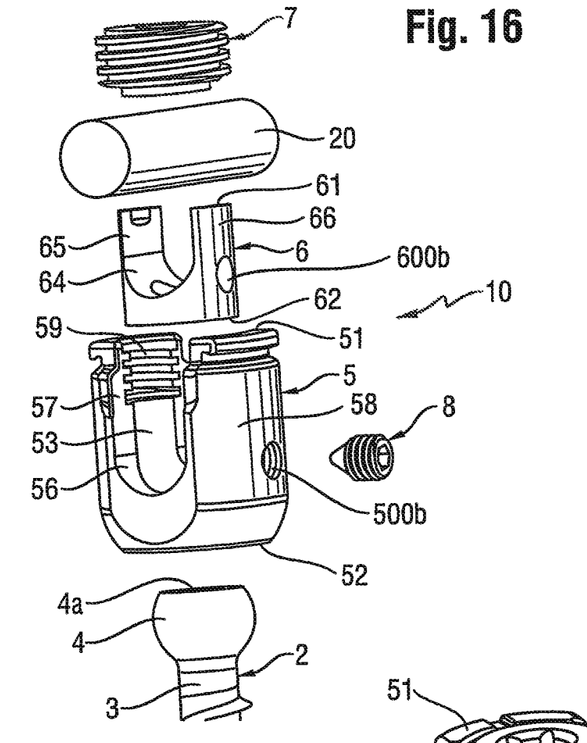
FIG. 16 shows a perspective exploded view of a polyaxial bone anchoring device according to a fifth embodiment.
Figure 17:
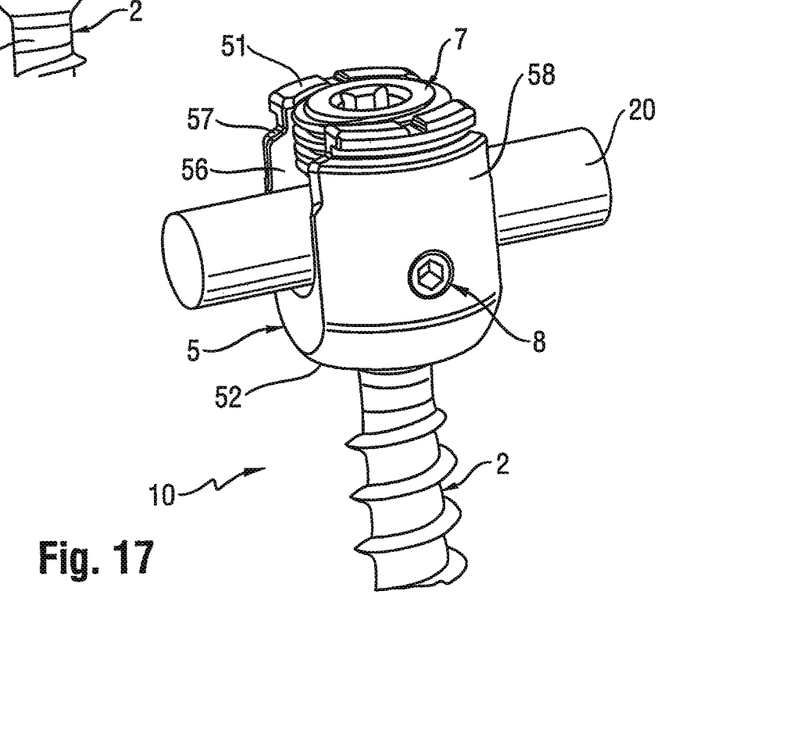
FIG. 17 shows the polyaxial bone anchoring device of FIG. 16 in an assembled state.
Figure 18:
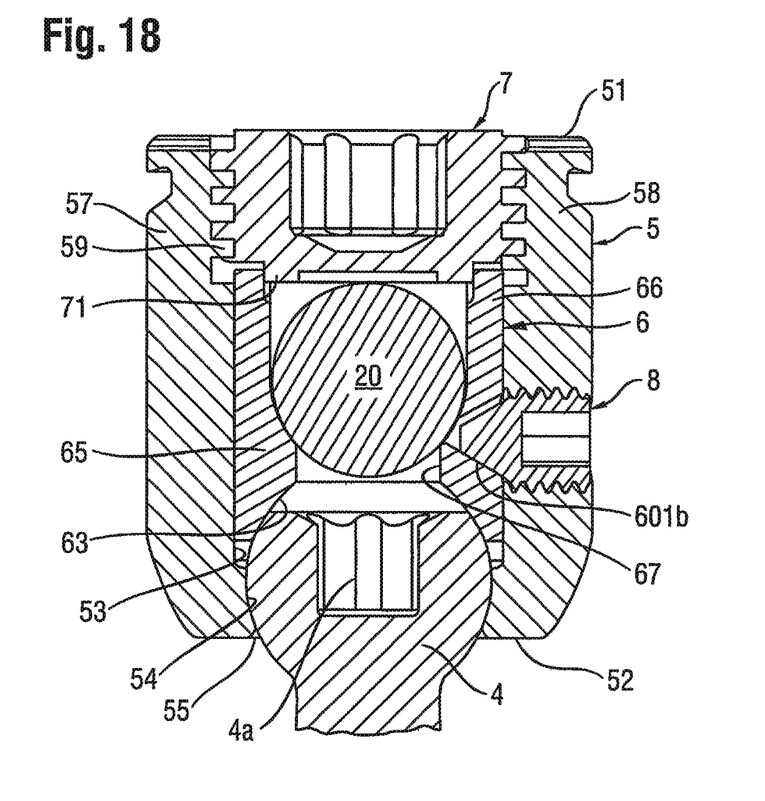
FIG. 18 shows a cross-sectional view of the polyaxial bone anchoring device according to the fifth embodiment in an assembled state.

In a fifth embodiment, shown in FIGS. 16 to 18, a bone anchoring device 10 may only include a single set screw 8, instead of two set screws 8 as described in the embodiments shown in FIGS. 1 to 4 and 12 to 15.

Figure 19:
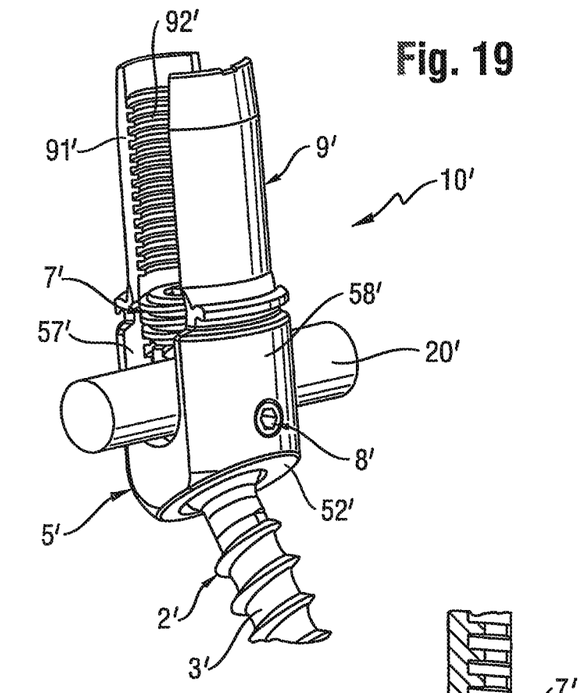
FIG. 19 shows a perspective view of a polyaxial bone anchoring device according to a sixth embodiment in an assembled state.
Figure 20:
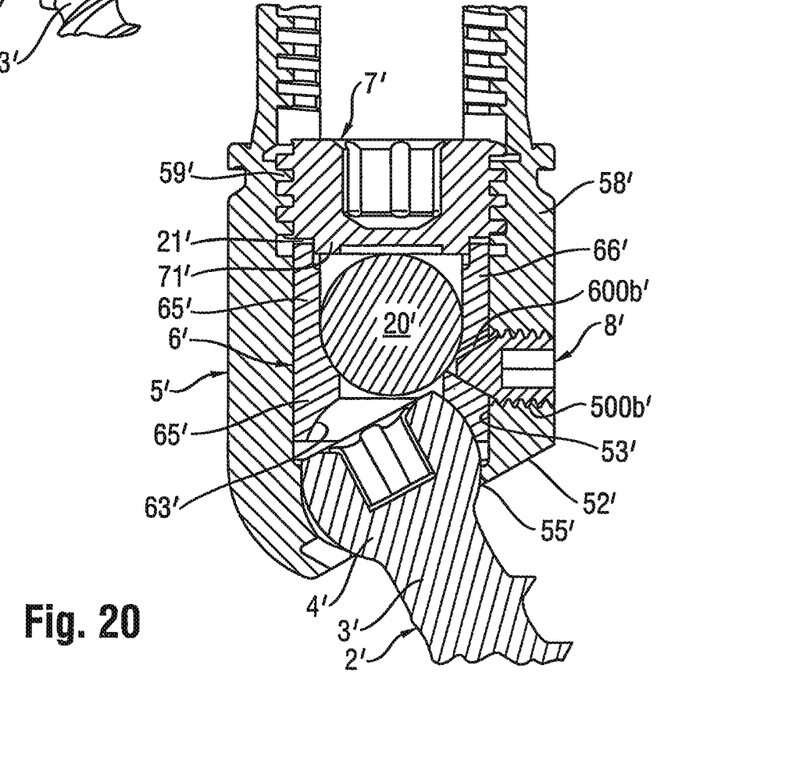
FIG. 20 shows a cross-sectional view of the polyaxial bone anchoring device according to the sixth embodiment in an assembled state.

In a sixth embodiment, shown in FIGS. 19 and 20, a bone anchoring device 10' also may only include one set screw 8 instead of two set screws 8 as described in the previous embodiments, and may include an inclined lower edge or asymmetrical bottom end as shown in FIGS. 12 and 13. All other parts may be the same or similar to the previously described embodiments.

The parts of the bone anchoring device according to embodiments of the invention may be made of a body-compatible material, such as a body-compatible metal, for example, titanium, of body-compatible metal alloys such as, for example, Nitinol, or from a body-compatible plastic material, such as, for example, polyether ether ketone (PEEK), or combinations thereof.

Usually, several bone anchoring devices are utilized for stabilizing bone parts or vertebrae with a rod. In use, the bone anchoring devices may be pre-assembled, as shown in FIG. 4. The anchoring elements may be screwed into or otherwise attached to the bone or vertebra. Then, the receiving parts are pivoted by applying a force greater than the friction force until each receiving part has a correct orientation for insertion of the rod. Due to the friction force, each receiving part is held in its adjusted angular position. Thereafter, the rod, which connects the bone anchoring devices, is inserted, and the set screws and/or the inner screw in some embodiments, are tightened to move the pressure element downwards to lock the head in the seat of the receiving part, so that the angular position of the anchoring element with respect to the receiving part is fixed. The rod is fixed by the inner screw.

The shapes of the through bores and/or bore holes of the embodiments described are not limited to the described forms. Also the angles of the tapers are not limited to the values described. Other shapes are also possible to achieve a downwardly directed force when the set screw or screws are screwed in.

For the anchoring element, various different kinds of anchoring elements can be used and combined with a receiving part. These anchoring elements may be, for example, screws with different lengths, with different diameters, cannulated screws, screws with different thread forms, nails, hooks, etc. In some embodiments, the head and the shaft of the anchoring elements can be separate parts which are connectable to each other.

The shape of the receiving part is also not limited to the embodiments shown. For example it is possible to have a recess allowing the rod to be introduced from a side of the receiving part instead of being introduced from the top, or a closed recess through which the rod is to be guided. In addition, various kinds of locking devices, including locking devices with two or more parts, outer nuts, outer caps, bayonet locking devices, or various other locking devices are also possible.

In a further modification, the receiving part may be configured to allow introduction of the anchoring element from the bottom end in some embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
an anchoring element having a shaft for anchoring in a bone and a head;
a receiving part having a first end and a second end, a channel for receiving a rod therein, a bore extending from the first end towards the second end, a seat for receiving the head, and at least one threaded through hole transverse to the bore;
a pressure element configured to be arranged in the bore and to exert pressure onto the head when the head and the pressure element are in the receiving part, such that the head is pivotable with respect to the receiving part and can be locked at an angle relative to the receiving part by the pressure element, the pressure element having at least one hole configured to at least partially align with the through hole of the receiving part; and
at least one set screw having a tapered portion and being configured to be inserted into the through hole of the receiving part;
wherein when the head and the pressure element are in the receiving part, the set screw is threadable into the through hole to a first position where the set screw engages the pressure element at the hole such that a first force is exerted by the pressure element onto the head that maintains the head at an adjustable angular position relative to the receiving part by friction prior to locking the head relative to the receiving part;
wherein the set screw is threadable into the through hole past the first position to a second position where the set screw engages the pressure element at the hole such that a second force greater than the first force is exerted by the pressure element onto the head; and
wherein a surface of the pressure element that engages the set screw in the first position is tapered with respect to a central axis of the receiving part, and the tapered portion of the set screw is configured to engage the pressure element at the hole.

2. The polyaxial bone anchoring device according to claim 1, wherein when the head and the pressure element are in the receiving part and the set screw is in the first position, an edge of the pressure element defining the hole is in contact with the set screw.

3. The polyaxial bone anchoring device according to claim 2, wherein when the set screw is in the first position, a central axis of the set screw and a central axis of the hole are offset along an axial direction of the receiving part, such that the set screw exerts a pressure on the pressure element by engaging the edge defining the hole to generate a defined friction force between the head and the pressure element.

4. The polyaxial bone anchoring device according to claim 1,
wherein the surface of the pressure element that engages the set screw forms a first angle with the central axis of the receiving part, and wherein an angle of the tapered portion of the set screw corresponds to the first angle.

5. The polyaxial bone anchoring device according to claim 4, wherein the first angle is between 30° and 60°.

6. The polyaxial bone anchoring device according to claim 1, wherein the hole of the pressure element is cylindrical.

7. The polyaxial bone anchoring device according to claim 1, wherein a cross-section of the hole of the pressure element is trapezoidal.

8. The polyaxial bone anchoring device according to claim 1, wherein at least two through holes are provided on the receiving part and at least two holes are provided on the pressure element.

9. The polyaxial bone anchoring device according to claim 8, wherein the through holes are offset by 180° in a circumferential direction of the receiving part, and wherein the holes are offset by 180° in a circumferential direction of the pressure element.

10. The polyaxial bone anchoring device according to claim 1, wherein the pressure element has a first end and a second end, a coaxial bore, a spherical segment-shaped recess at the second end, and a cylindrical or U-shaped recess at the first end, wherein the cylindrical or U-shaped recess is configured to be aligned with a recess of the receiving part when the pressure element is in the receiving part.

11. The polyaxial bone anchoring device according to claim 1, wherein the receiving part comprises an asymmetric end portion for allowing a greater pivot angle of the anchoring element to one side when the head is in the receiving part.

12. The polyaxial bone anchoring device according to claim 1, wherein the set screw comprises a threadless portion for engaging the hole of the pressure element.

13. The polyaxial bone anchoring device according to claim 12, wherein the threadless portion of the set screw is tapered.

14. The polyaxial bone anchoring device according to claim 1, wherein the set screw is configured to be advanced in the through hole of the receiving part to the second position to lock the angular position of the head relative to the receiving part.

15. A method of coupling a rod to a bone or vertebra via a polyaxial bone anchoring device, the polyaxial bone anchoring device comprising an anchoring element having a shaft for anchoring in a bone and a head, a receiving part having a first end and a second end, a channel for receiving the rod therein, a bore extending from the first end towards the second end, a seat for receiving the head, and at least one threaded through hole transverse to the bore, a pressure element configured to be arranged in the bore and to exert pressure onto the head when the head and the pressure element are in the receiving part, such that the head is pivotable with respect to the receiving part and can be locked at an angle relative to the receiving part by the pressure element, the pressure element having at least one hole configured to at least partially align with the through hole of the receiving part, and at least one set screw configured to be inserted into the through hole of the receiving part, the method comprising:
threading the set screw in the through hole of the receiving part to a first position where the set screw is fixedly retained in the receiving part and engages an inserted pressure element at the hole, such that a first force is exerted by the pressure element onto the head of a connected anchoring element that maintains the head at an adjustable angular position relative to the receiving part by friction;
further threading the set screw into the through hole past the first position to a second position where the set screw engages the pressure element at the hole such that a second force greater than the first force is exerted by the pressure element onto the head;
inserting the anchoring element into a bone or vertebra;
adjusting the angular position of the receiving part relative to the anchoring element;

inserting a rod into the channel of the receiving part and the channel of the pressure element; and locking the angular position of the receiving part relative to the anchoring element and a position of the rod relative to the receiving part.

16. The method of claim 15, further comprising:

connecting the anchoring element to the receiving part by positioning the head in the seat;

inserting the pressure element into the bore; and inserting the set screw into the through hole of the receiving part.

17. The method of claim 15, wherein the bone anchoring device further comprises a fixation element, the method further comprising advancing the fixation element into the channel, such that the fixation element exerts pressure on the rod, the rod exerts pressure on the pressure element, and the pressure element exerts pressure onto the head of the anchoring element, to simultaneously lock the angular position of the receiving part relative to the anchoring element and the position of the rod relative to the receiving part.

18. The method of claim 15, further comprising:

advancing a fixation element into the channel to lock the position of the rod relative to the receiving part.

19. The method of claim 15, wherein the hole of the pressure element extends through or a majority of a distance through a leg of the pressure element.

20. A polyaxial bone anchoring device comprising:

an anchoring element having a shaft for anchoring in a bone and a head;

a receiving part having a first end and a second end, a channel for receiving a rod therein, a bore extending from the first end towards the second end, a seat for receiving the head, and at least one threaded through hole transverse to the bore;

a pressure element configured to be arranged in the bore and to exert pressure onto the head when the head and the pressure element are in the receiving part, such that the head is pivotable with respect to the receiving part and can be locked at an angle relative to the receiving part by the pressure element, the pressure element having at least one hole extending through or a majority of a distance through a leg of the pressure element and being configured to at least partially align with the through hole of the receiving part; and at least one set screw configured to be inserted into the through hole of the receiving part;

wherein when the head and the pressure element are in the receiving part, the set screw is threadable into the through hole to a first position where the set screw engages the pressure element at the hole such that a first force is exerted by the pressure element onto the head that maintains the head at an adjustable angular position relative to the receiving part by friction prior to locking the head relative to the receiving part; and wherein the set screw is threadable into the through hole past the first position to a second position where the set screw engages the pressure element at the hole such that a second force greater than the first force is exerted by the pressure element onto the head.

* * * * *